United States Patent [19]

Schiller

[11] Patent Number: 4,569,080
[45] Date of Patent: Feb. 4, 1986

[54] FINGERPRINT IMAGE REFINEMENT

[75] Inventor: Michael Schiller, Riverdale, N.Y.

[73] Assignee: Fingermatrix, Inc., North White Plains, N.Y.

[21] Appl. No.: 507,067

[22] Filed: Jun. 23, 1983

Related U.S. Application Data

[63] Continuation-in-part of Ser. No. 396,813, Jul. 9, 1982, abandoned.

[51] Int. Cl.[4] ............................................. G06K 9/36
[52] U.S. Cl. ......................................... 382/4; 356/71
[58] Field of Search ..................... 382/2, 4, 5; 356/71; 350/485

[56] References Cited

U.S. PATENT DOCUMENTS

| | | | |
|---|---|---|---|
| 3,443,098 | 5/1969 | Lewis | 350/485 |
| 3,511,571 | 5/1970 | Ogle | 382/4 |
| 3,882,462 | 5/1975 | McMahon | 356/71 |
| 4,120,585 | 10/1978 | Depalma et al. | 356/71 |
| 4,322,163 | 3/1982 | Schiller | 356/71 |

OTHER PUBLICATIONS

Claassen et al., "Fingertip Orienting and Ridge Viewing Apparatus", *IBM Technical Disclosure Bulletin*, vol. 8, No. 3, 1965, pp. 435-436.

Primary Examiner—Leo H. Boudreau
Attorney, Agent, or Firm—McAulay, Fields, Fisher, Goldstein & Nissen

[57] ABSTRACT

In an optical fingerprint image processing apparatus a light beam is scanned across a finger placed against a transparent platen in order to provide a reflected modulated light beam carrying fingerprint information. The modulated light beam is imaged and the image is intercepted by an array of photo receptors that detect the image and convert the optical signal into electrical signals. The improvement is in placing a diffuser element, which may be a ground glass wafer, in the interrogating light beam. The diffusion of the light beam acts as an effective filter to eliminate the higher spatial frequency components of the optical image and thus provide a fingerprint image having improved continuity.

10 Claims, 6 Drawing Figures

FINGERPRINT IMAGE REFINEMENT

REFERENCE TO RELATED APPLICATIONS

This application is a continuation-in-part of application Ser. No. 396,813 filed July 9, 1982 and entitled Fingerprint Image Refinement, now adandoned.

BACKGROUND OF THE INVENTION

This invention relates in general to finger identification and to finger image processing apparatus.

More particularly, this invention relates to a system for improving the optical image obtained from reflecting an interrogating light beam off the finger object of an individual.

U.S. Pat. No. 4,322,163 issued Mar. 30, 1982, describes the optical and mechanical component of the finger identification system which provides an optical scan of a subject's finger placed against a platen to provide a modulated reflected light beam that is imaged at an array of photoelectric detectors.

The platens described therein include a glass platen with an anti-reflective coating on the finger receiving surface (hereinafter, hard coat platen) and various platens some of which include a reflective surface. It has been found that the images provided by the light reflected from the finger object on these platens contains details or distortions which break up the smooth continuous pattern of ridge flow.

Specifically, the hard coat platen produces an image with high spatial frequency components that require compensation in the downstream electronic image processing system. The detailed angularity and breaks provided by the image from the hard coat platen makes it more difficult to extract the continuous pattern which has to be analyzed.

The high spatial frequency components of the image tend not to be repeatable so that the seeming detailed precision of this image is in fact a distortion of the underlying repeatable patterns.

It is important that any finger identification system be usable with as wide a range of population as possible. Any such system has to deal with individuals whose fingers range from having a relatively smooth surface, where there are relatively minor ridges and valleys, to individuals who have pronounced ridge and valley configurations. It has been found that where the resilient platen is used, certain individuals with pronounced ridge and valley demarcations provide so much modulation that the image is distorted.

Accordingly, it is a purpose of this invention to provide a mechanism to compensate for and minimize these distortions and details.

It is important that the compensation technique avoid degrading the effectiveness and value of this system to provide the desired finger image pattern. It is also important that the compensation technique avoid a significant increase in the cost of the apparatus involved. The advantage obtained by being able to include a broader population should not be offset by either a loss of inclusion of other individuals or the addition of costs in excess of the advantages obtained. Accordingly, it is a further object of this invention to achieve the above stated object within the constraints of avoiding system degradation and avoiding substantial increased costs of equipment or of processing time.

Most importantly, it is an object of this invention to provide an improved optical image of the finger that will simplify the downstream electronic porcessing and thus provide an improved trade-off between lower cost and faster processing.

The disclosure of U.S. Pat. No. 4,322,163 is incorporated herein by reference to simplify the description of the improvement involved herein.

BRIEF DESCRIPTION

In brief, the improvement of this invention involves the insertion of a light diffuser element in the interrogating light beam upstream of the platen. The result is to provide incident light, on the finger object being interrogated, which is partially but not completely diffused.

THE DRAWINGS

FIG. 1 is a schematic optical diagram of an embodiment of the appartus, similar to that shown in FIG. 3 of the U.S. Pat. No. 4,322,163, but including the improvement feature of this invention.

FIG. 2 is a schematic cross sectional view of a resilient platen. The platen of FIG. 2 is comparable to the FIG. 7 platen in the referenced patent. It should be understood that the representation in FIG. 2 is highly schematic and represents what is believed to be the relation between platen and finger ridges and valleys.

FIG. 3 is an enlarged illustration of a typical glass diffuser element having a ground surface.

FIGS. 4A and 4B schematically illustrate and contrast the finger image obtained with and without the device of this invention. FIG. 4A illustrates a finger image using the prior art system. FIG. 4B illustrates the same individual's finger with the improvement of this invention.

FIG. 5 is a view similar to that of FIG. 2 illustrating the hard coat platen, that is, a glass platen, having an anti-reflective coating.

DESCRIPTION OF THE PREFERRED EMBODIMENTS

Figure 1:
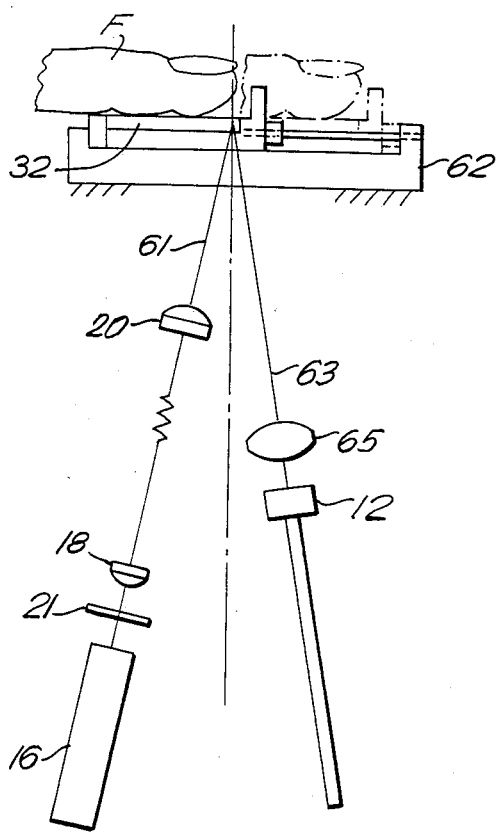

As illustrated in the FIGS., a light source such as the laser 16 provides a light beam which is appropriately shaped by lens 18 and 20 to provide an interrogating light beam 61 that impinges against a finger F which is held against a platen 32. In the embodiment illustrated, the platen 32 is mounted on a carriage 62 which permits translational movement of the finger F and platen 32 (from left to right as shown in FIG. 1) so that the finger is scanned by the light beam 61. As described in the referenced patent, the finger and platen 32 may be stationary while the interrogating light beam is displaced to scan the finger. The presently preferred embodiment incorporates the latter scheme. However, the scheme employed is substantially irrelevant to the improvement of this invention.

The reflected light beam 63 is modulated with finger information by the finger object F. A lens 65 provides the finger image which is detected by an array 12 of photodetectors. A synchronized electronic scan of the detectors 12 operates at a rapid rate compared to the optical scan, so that a series of picture elements (pixels) are developed from the finger image for further processing.

Figure 2:
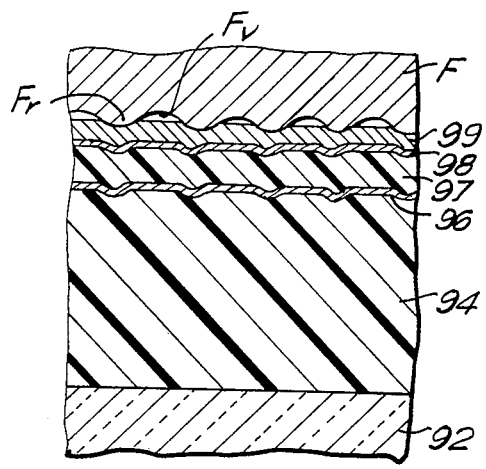

FIG. 2 illustrates a resilient platen 32 which is comprised of a relatively substantial transparent glass substrate 92 that is nominally 6 mm thick, a first epoxy layer 94 which is 0.25 mm thick, a second epoxy layer 97 which is 0.050 mm thick and a lacquer layer 99 which is 0.025 mm thick. The two silver layers 96 and 98 are approximately 3,000 Angstroms thick. The ridge structure $F_r$ of the fingers causes the deformable resilient epoxy layer 94 and 97 to deflect, and thus to carry the relective layer 96 with it, so that, as shown, the reflective layer 96 has relatively flat portions corresponding to the valleys $F_v$ of the finger and relatively rounded portions corresponding to the ridges $F_r$ of the finger. As shown in FIG. 2, the incident light 61 under the valleys relects as an incident light beam 63 that has an angle of reflection substantially equal to the angle of incidence. The reflected beam 63 have relatively little scatter. This light beam 63 is imaged as a light zone for detection at the array 12. By contrast, the rounded portions of the reflected layer 96, corresponding to the finger ridges $F_r$, cause the reflected light to scatter substantially more than is the case under the finger valley $F_v$ zones. However, the amount of scatter from under the ridges, although substantially greater than the amount of scatter from under the valleys, is still substantially within the optical aperture of the lens 65.

As described in the referenced patent, the image at the image plane of the lens 65 is a bright light image since it is substantially an image of the reflective layer 96. Whatever difference of light intensity there is at the image plane is too bright at both ridge and valley zones to be useful. Accordingly, the array 12 is positioned a short distance off the image plane (for example, 1 or 2 mm from the image plane). At such a position, the scattered light from the rounded areas under the ridges is not properly focused thereby providing contrast in ridge and valley zones.

Specifically, downstream from the image plane, the defocused ridges appear dark while the valley zones remain bright. Upstream, for reasons that are not entirely clear to applicant, the valleys, as expected, remain substantially as bright as at the image plane but the ridges achieve a light intensity substantially brighter than that of the valleys and substantially brighter than at the image plane.

A diffuser element 21 is positioned in the interrogating light beam 61 and preferably is positioned immediately adjacent to the beam from the laser element 16. A standard ground glass diffuser is employed and the result is to create an appreciable amount of crossover of the light rays within the interrogating beam 61. However, the diffusion is not so great as to cause complete diffusion and loss of directivity for most of the light within the light beam.

What has been found is that in the absence of the diffuser element 21, the ridge image at the array 12 becomes distorted for certain individuals. For most individuals, this system operates equally as well with or without the diffuser element 21. But for certain individuals who have a pronounced ridge to valley height in their finger, there is a degree of ridge image breakup and even some twinning of the ridge image at the array 12. This phenomenon limits the scope of utility of the apparatus. However, the addition of the diffuser element 21 obviates this problem wihtout losing any of the population having a relatively smooth (that is, low ridge to valley height) finger surface.

Figure 4A:
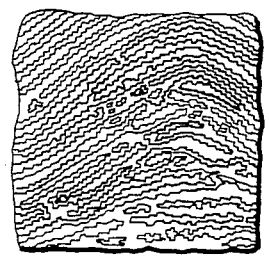
Figure 4B:
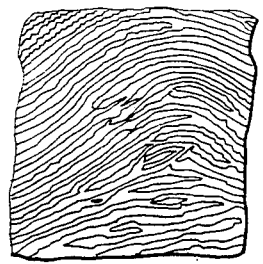

An example is illustrated schematically in FIGS. 4A and 4B. FIG. 4A shows the kind of broken up image that occurs in connection with certain individuals when the FIG. 1 system is employed without the diffuser element 21. FIG. 4B shows the improved result with the diffuser element 21. FIGS. 4A and 4B are taken from the same individual. The difference between the two figures can be noted with the eye. However, the effective difference between the two figures in terms of any automatic processing apparatus is far more significant than might appear to the eye. The unwanted breaks that are shown in FIG. 4A tend to confound any enrollment or identification apparatus because these breaks do not reflect legitimate minutia. One of the important consequences of this is that these breaks are not repeatable and the individual who is enrolled with the FIG. 4A input fingerprint will not be reliably identified at subsequent times. In order to get reliable and repeatable identification, it is important that only the classical minutia be identified and enrolled.

Figure 3:
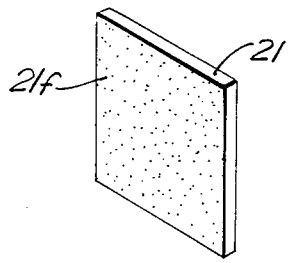

The diffuser element 21 is a small glass plate having a ground surface 21f as indicated in FIG. 3. In one embodiment that has been tested, the dispersion plate 21 has a grain size of ten micrometers in diameter. It is not believed that there is anything critical about the grain size on the ground glass surface 21f except too fine a grain size might create so much diffusion as to seriously degrade the interrogating beam and too great a grain size would generate too little diffusion to create the results desired. Also, it is not believed that the material of the plate 21 is of any great significance.

Figure 5:
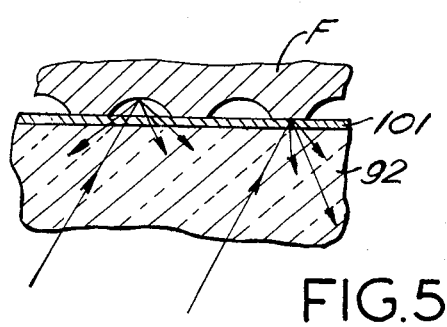

FIG. 5 illustrates a platen 92 for which the diffuser 21 provides a substantial improvement in the FIG. 1 system. This hard coat platen 92 has an anti-reflective coating 101 on the finger touching surface. This platen is illustrated in FIG. 8 of the reference U.S. Pat. No. 4,532,163 and is described in detail therein. However, when the invention is employed in connection with such an anti-reflective coated platen, the position of the array 12 has to be displaced from the image plane of the lens 65 in order for the diffuser 21 to have the desired effect. Accordingly, both the FIG. 2 resilient, deformable platen and the anti-reflectant glass platen may be used with the improved system of this invention incorporating the diffuser element 21.

The important effect of using the diffuser 21 with the hard coat platen of FIG. 5 is to filter out certain sharp discontinuities so as to provide a more continuous image at the plane of the photo-responsive elements 12. Thus, the diffuser 21 provides a high spatial frequency filtering. As a consequence, the downstream electronics can be a simpler, less expensive and more effective processing system. The result is to improve the image provided for all of the population.

By contrast, the advantage initially obtained in using the diffuser 21 with the resilient platen of FIG. 2 was to compensate for observed twinning effects in the image that occurred with certain individuals. The resilient platen of FIG. 2 provided much of the high frequency filtering so that the diffuser 21 was useful primarily to bring into the system certain individuals whose image was, for reasons not fully understood, distorted by use of the resilient platen.

What has now been found is that this diffuser element 21 has a somewhat different type of advantage when used with the hard coat platen of FIG. 5. It provides some of the high frequency filtering advantages that are obtained with the resilient platen without generating the twinning effect or distortions that have occurred with certain individuals using the resilient platen. As a consequence, this diffuser element 21 has the very important results of making it possible to use the simpler hard coat platen of FIG. 5 in systems where it was otherwise thought necessary to use the resilient platen of FIG. 2.

What I claim is:

1. In an optical fingerprint image processing apparatus wherein a fingerprint object on a platen is optically scanned by an interrogating light beam to provide a reflected light beam modulated with the fingerprint information and wherein the modulated light beam is imaged by an imaging lens and an array of photo detectors is positioned downstream from the lens to receive and detect the image formed, the improvement comprising:

a diffuser element positioned within the interrogating light beam to partially diffuse said beam and to provide an interrogating light beam at the fingerprint object which is sufficiently diffused to eliminate the higher spatial frequency components of the reflected image;

whereby over-modulation components of the reflected image are avoided.

2. The improvement of claim 1, wherein said platen has a transparent substrate and a deformable resilient layer on the finger receiving surface thereof, said layer being responsive to an applied finger to provide the fingerprint object, said deformable layer including a reflective layer to provide the fingerprint object as a reflective object.

3. The improvement of claim 2, wherein said diffuser element has a diffusing surface with a grain size approximately ten micrometers in diameter.

4. The improvement of claim 1, wherein said platen has a transparent substrate and an anti-reflective coating on the finger receiving surface thereof.

5. The improvement of claim 4, wherein said diffuser element has a diffusing surface with a grain size approximately ten micrometers in diameter.

6. The improvement of claim 1, wherein said diffuser element has a diffusing surface with a grain size approximately ten micrometers in diameter.

7. In the method of optically processing a fingerprint image in which a fingerprint object is optically scanned by an interrogating light beam to provide a reflected light beam modulated with the fingerprint information and wherein the modulated light beam is imaged by an imaging lens and an array of photodetectors is positioned downstream from the lens to receive and detect the image formed, the improvement comprising the step of:

partially diffusing the interrogating light beam, the partial diffusion being sufficient to eliminate the higher spatial frequency components of the fingerprint image carried by the reflected light beam, whereby over-modulation components of the reflected image are avoided.

8. The method fo claim 7, wherein said step of diffusing is insufficient to substantially degrade the interrogating light beam.

9. The method of claim 7, wherein the fingerprint object is formed from a finger placed against a platen and wherein the interrogating light beam is modulated by differential scattering of the light reflected respectively from beneath the valley and ridge zones.

10. The method of claim 7, wherein the fingerprint object is formed from a finger placed against a platen having an anti-reflective coating on the finger receiving surface thereof.

* * * * *